(12) United States Patent
Mossman

(10) Patent No.: US 10,677,926 B2
(45) Date of Patent: Jun. 9, 2020

(54) SENSORY AUGMENTATION SYSTEM

(71) Applicant: Guy E Mossman, Mount Pleasant, SC (US)

(72) Inventor: Guy E Mossman, Mount Pleasant, SC (US)

( * ) Notice: Subject to any disclaimer, the term of this patent is extended or adjusted under 35 U.S.C. 154(b) by 399 days.

(21) Appl. No.: 15/871,396

(22) Filed: Jan. 15, 2018

(65) Prior Publication Data

US 2019/0219704 A1  Jul. 18, 2019

(51) Int. Cl.
| | |
|---|---|
| *A63B 1/00* | (2006.01) |
| *G01S 19/19* | (2010.01) |
| *G01S 19/37* | (2010.01) |
| *G06F 3/01* | (2006.01) |
| *G06F 3/16* | (2006.01) |
| *G01S 19/52* | (2010.01) |
| *G01S 19/42* | (2010.01) |
| *G01C 21/20* | (2006.01) |
| *G09B 21/00* | (2006.01) |
| *B63B 49/00* | (2006.01) |
| *G06F 1/16* | (2006.01) |

(52) U.S. Cl.
CPC .............. *G01S 19/19* (2013.01); *A63B 1/00* (2013.01); *B63B 49/00* (2013.01); *G01C 21/203* (2013.01); *G01S 19/37* (2013.01); *G01S 19/42* (2013.01); *G01S 19/52* (2013.01); *G06F 1/163* (2013.01); *G06F 3/011* (2013.01); *G06F 3/016* (2013.01); *G06F 3/167* (2013.01); *G09B 21/007* (2013.01); *A63B 2220/12* (2013.01)

(58) Field of Classification Search
CPC .......... G01S 19/19; G01S 19/37; G01S 19/42; G01S 19/52; A63B 1/00; A63B 2220/12; B63B 49/00; G01C 21/203; G06F 1/163; G06F 3/011; G06F 3/016; G06F 3/167; G09B 21/007
USPC ....................................................... 701/491
See application file for complete search history.

(56) References Cited

U.S. PATENT DOCUMENTS

| | | |
|---|---|---|
| 8,552,847 B1 | 10/2013 | Hill |
| 9,256,281 B2 | 2/2016 | Ur |
| 9,726,501 B2 * | 8/2017 | Benel ...................... G01C 21/20 |
| 9,734,678 B2 | 8/2017 | Hill |

* cited by examiner

*Primary Examiner* — Gertrude Arthur Jeanglaude
(74) *Attorney, Agent, or Firm* — Merek, Blackmon & Voorhees LLC

(57) ABSTRACT

A programmable control unit including a gps receiver and having the capability of receiving a plurality user-programmable waypoints and calculating distance and direction for each of the programmable waypoints. The programmable control unit further including a mechanism capable of producing a signal to assist a user to maintain a course toward a waypoint wherein the programmable control unit may be programmed by the user to set the frequency of the signal.

20 Claims, 4 Drawing Sheets

TACTICAL HEADBAND

ENCLOSURE

TACTICAL HEADBAND

SENSORY AUGMENTATION SYSTEM

FIELD OF THE INVENTION

The present invention is directed to a system including an apparatus and a method for augmenting sensory perception to overcome visual impairment. This invention is particularly suited for use in navigation during sailboat racing, kayaking, paddleboarding, canoeing, hiking, bicycling, powerboating and swimming.

BACKGROUND OF THE INVENTION

When navigation is conducted in a manner where the individual is unable or does not want to read a display, providing directions by sound is an alternative solution. For example, the use of voice directions is common in automobile global positioning systems (gps) where there are marked lanes and streets. However, it would also be useful to have a navigation aid that does not require viewing a map or screen in areas where there are no street signs or lanes such as on a body of water or in a forest.

Furthermore, it would be advantageous for visually impaired individuals in sports activities such as sailboat racing to have a navigation aid that does not require sight. Currently visionally impaired individuals require a sighted individual to assist them with navigation in sailboating. Therefore, a navigation system that can be used by a sight impaired individual to provide navigation assistance to reach a destination without relying on someone else would provide greater independence for the user.

In view of the foregoing it can be seen that there is a need for a new navigation device to provide directional assistance without the need for visually observing landmarks or a display screen or reliance on others.

OBJECTS AND SUMMARY OF THE INVENTION

An object of a preferred embodiment of the present invention is to provide a novel and unobvious method and/or apparatus for providing navigational assistance.

Another object of a preferred embodiment of the present invention is to provide an apparatus that is designed to provide navigational assistance without requiring the user to consult a display screen.

A further object of a preferred embodiment of the present invention is to provide tactile sensory augmentation to provide directional assistance.

Yet another object of a preferred embodiment of the present invention is to provide a wearable apparatus that can indicate direction changes by applying tactile pressure or vibration to areas on the wearer's body.

Still a further object of a preferred embodiment of the present invention is to provide an apparatus in the form of headband that includes devices to exert pressure or vibration to indicate a direction of travel to the wearer.

Yet another object of the invention is to provide an audible signal to indicate course directions to the user.

Still another object of the invention is to provide a bone transmitter that can be worn and includes a tactile pressure or vibration device for use in indicating course directions.

Another object of a preferred embodiment of the present invention is to provide a programmable directional aid.

Yet another object of the invention is to provide a system combining radio signals and a gps unit and a magnetometer and an accelerometer to facilitate navigation.

Still another object of the invention is to provide a system that is networked that can be used by a group of participants in a racing event to determine speed, distance and direction information between the participants so that collisions between the participants can be avoided.

It must be understood that no one embodiment of the present invention need include all the aforementioned objects of the present invention. Rather, a given embodiment may include one or none of the aforementioned objects. Accordingly, these objects are not to be used to limit the scope of the claims of the present invention.

In summary, one embodiment of the present invention is directed to a programmable control unit including a GPS receiver and having the capability of receiving a plurality of user programmable waypoints and calculating distance and direction for each of the programmable waypoints. The programmable control unit further including a mechanism capable of producing a signal to assist a user to maintain a course toward a waypoint wherein the programmable control unit may be adjusted by the user to set the frequency of the signal. The programmable control unit also includes a radio transceiver for communicating with other programmable control units and sharing speed, direction and proximity information.

Another embodiment includes a method for providing direction of travel information to a user including providing a wearable device having sensory augmentation features for indicating direction of travel and providing a control unit having GPS capability and a compass and configuring the control unit to retain at least a first programmable waypoint and calculating a distance from the control unit to the first programmable waypoint and configuring the control unit to determine a direction of travel necessary to reach the first programmable waypoint, and configuring the control unit to send a radio signal to the wearable device for activating at least one of the sensory augmentation features to assist a user to maintain a course toward a waypoint.

DETAILED DESCRIPTION OF THE PREFERRED EMBODIMENTS OF THE INVENTION

The most preferred form of the invention will now be described with reference to FIGS. 1-4. The appended claims are not limited to the most preferred form and no term used herein is to be given a meaning other than its ordinary meaning unless otherwise stated.

Figure 1:
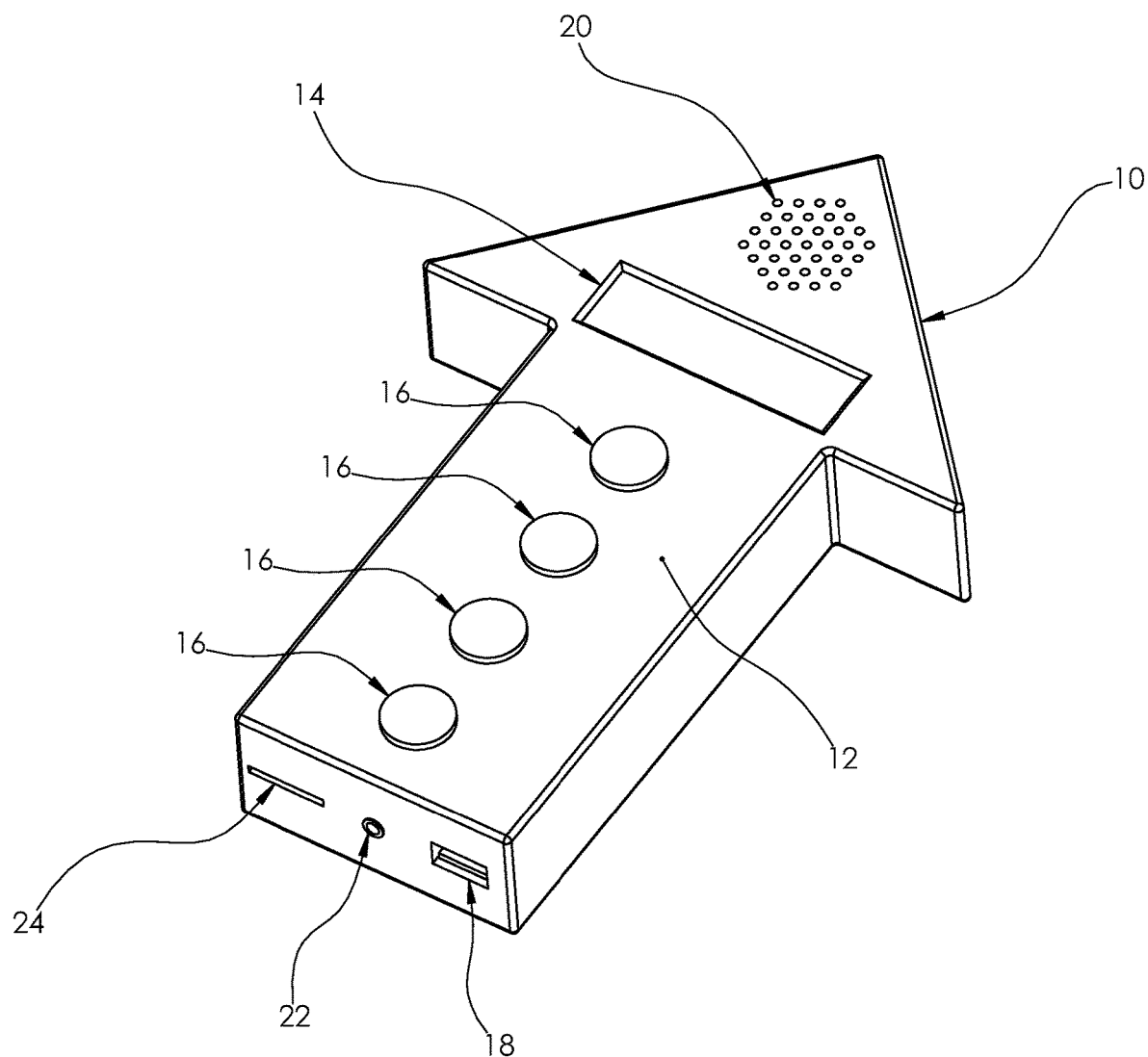
FIG. 1 shows the control unit.

A control unit 10 is shown in FIG. 1. The control unit 10 is preferably buoyant and has a waterproof shell formed substantially rigid material such as plastic or metal. The control unit 10 would be preferably of a size that could be handheld, but could also be mounted on a surface with adhesive or fasteners. The top face 12 of the control unit 10 includes a display screen 14 for displaying inputs and navigation information such as a course or a heading or a map displaying the course and heading. The display screen 14 is preferably an LCD screen. The top face 12 further includes input areas 16 which may be buttons, switches, potentiometers or touch sensitive areas which can be used to load navigational information such as waypoints and calibrate the control unit 10. The control unit 10 preferably contains a USB port 18, a battery, an audio output such as a speaker 20 and a headphone jack 22 and an SD card slot 24.

The control unit 10 is preferably waterproof and buoyant. Power is preferably provided to the control unit 10 by a 3.7 volt lithium ion battery which may be recharged through the USB port 18. Alternatively, or additionally power could be supplied by a power source separated from the control unit 10 and could be a battery worn on a belt, helmet, a life jacket or a boat and wired to the control unit 10. To assist those users with impaired vision, the control unit 10 preferably includes an audio based menu system and the input areas 16 can provide a vibration or tone so the user would know an input area 16 was activated when contacted. The control unit 10 further includes an LCD display screen 14 showing menus and calibration features. The display screen 14 is preferably a NMEA compatible display for use with multiple port NMEA interfaces and the LCD display 14 can also be mirrored on other displays.

The control unit 10 preferably contains a circuit board having a micro controller and components that provide audio amplification, Bluetooth capability, a Global Positioning System (GPS), a compass and power regulation.

Figure 2:
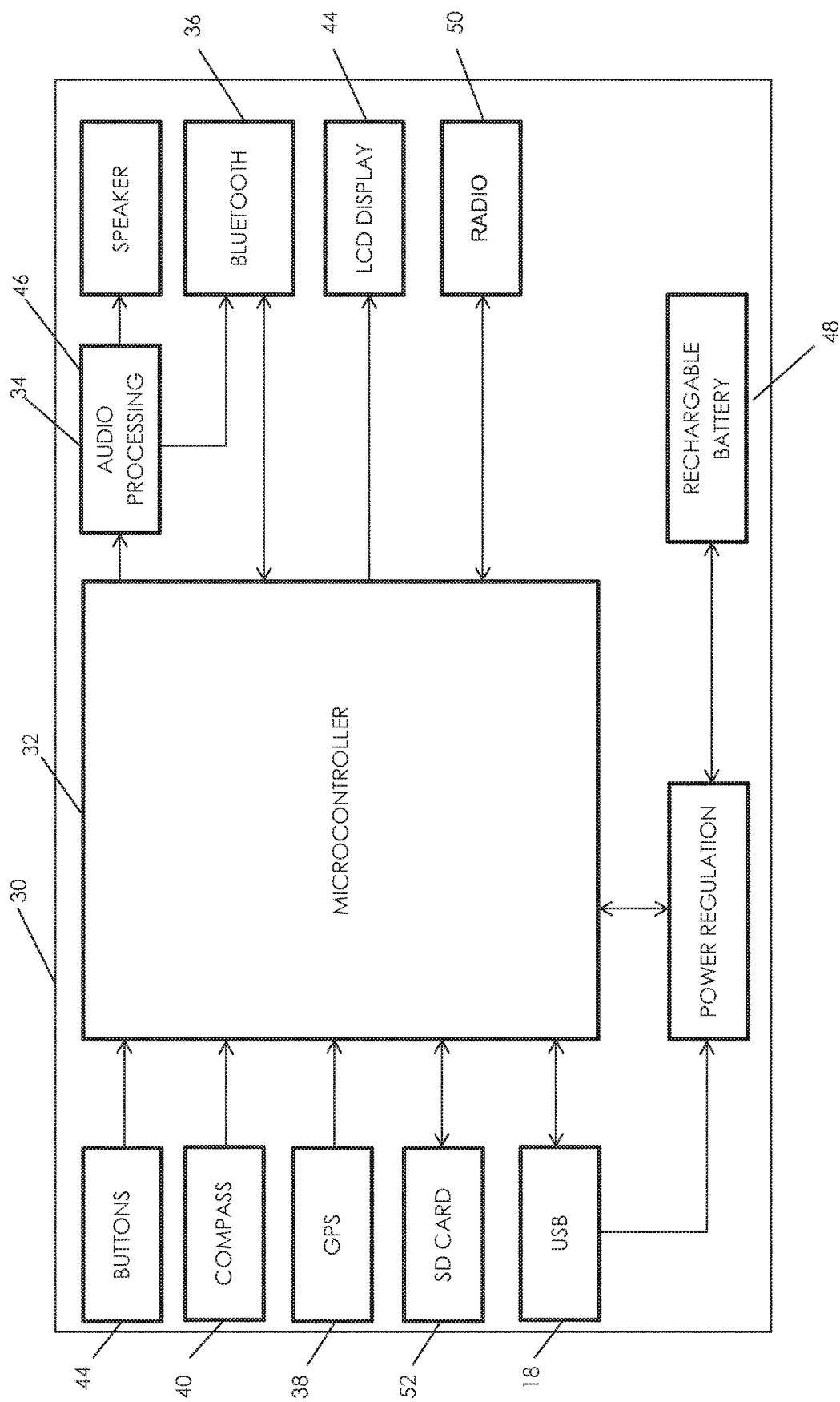
FIG. 2 is a block diagram of the microcontroller and components.

A block diagram of a circuit board 30 is shown in FIG. 2 illustrating the relationships of the micro controller 32 and the components that provide USB input 18, audio amplification 34, Bluetooth capability 36, a Global Positioning System (GPS) unit 38 having a 5 Hz update rate, a compass 40, power regulation 42, display screen controls 44, an audio output processor 46, a rechargeable battery 48, a 900 MHz radio transceiver 50 and an SD card 52 which may be removable.

The compass is provided by a chip module that includes a magnetometer and an accelerometer and would preferably have a direction accuracy of at least 0.1 degrees.

The system can preferably use separate SD cards 52 having different programming depending on the application, i.e., sailboat racing, bicycling, hiking or swimming. The USB port 18 allows interaction with the SD card 52 to control the SD card programming, diagnostics and settings.

Figure 3:
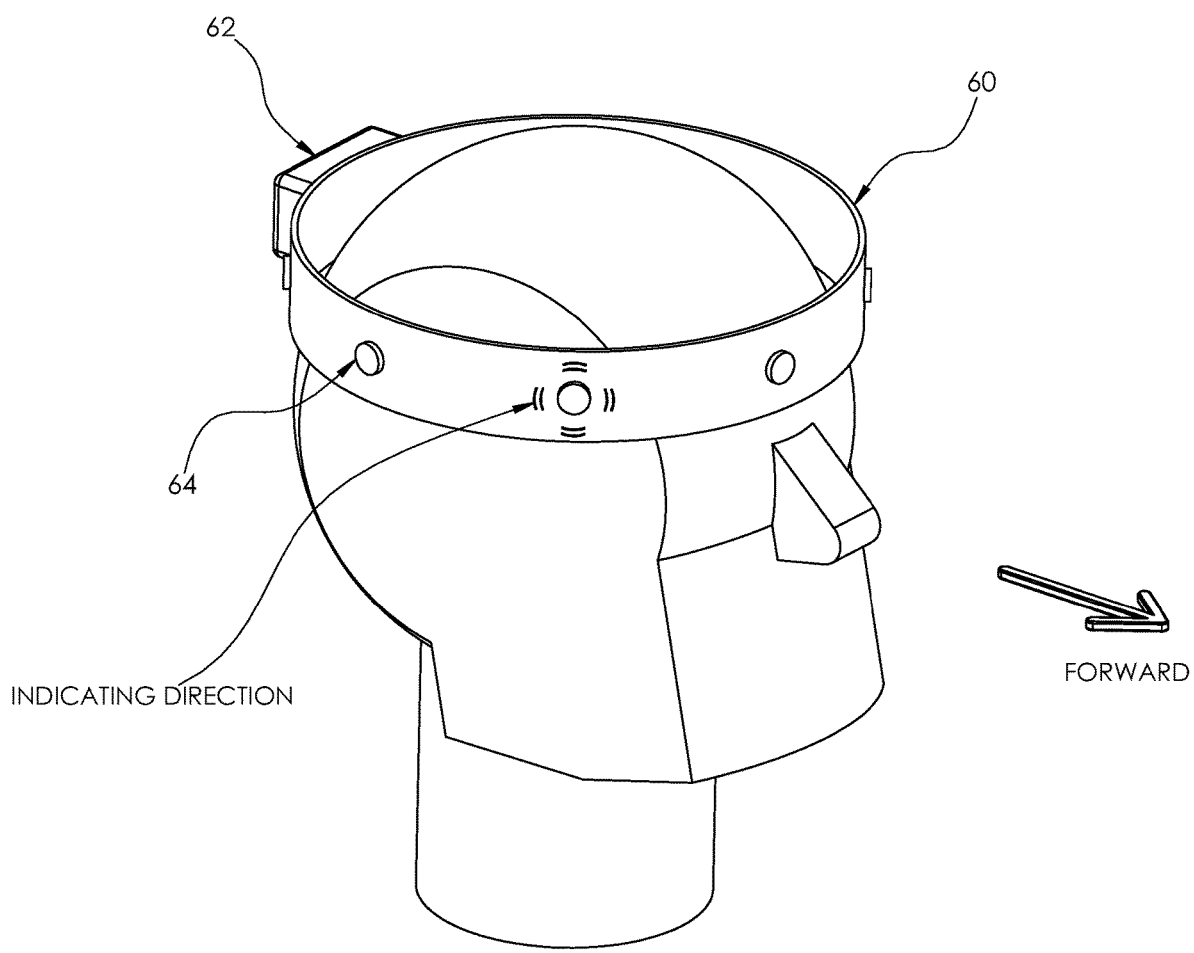
FIG. 3 is a schematic view of a headband.
Figure 4:
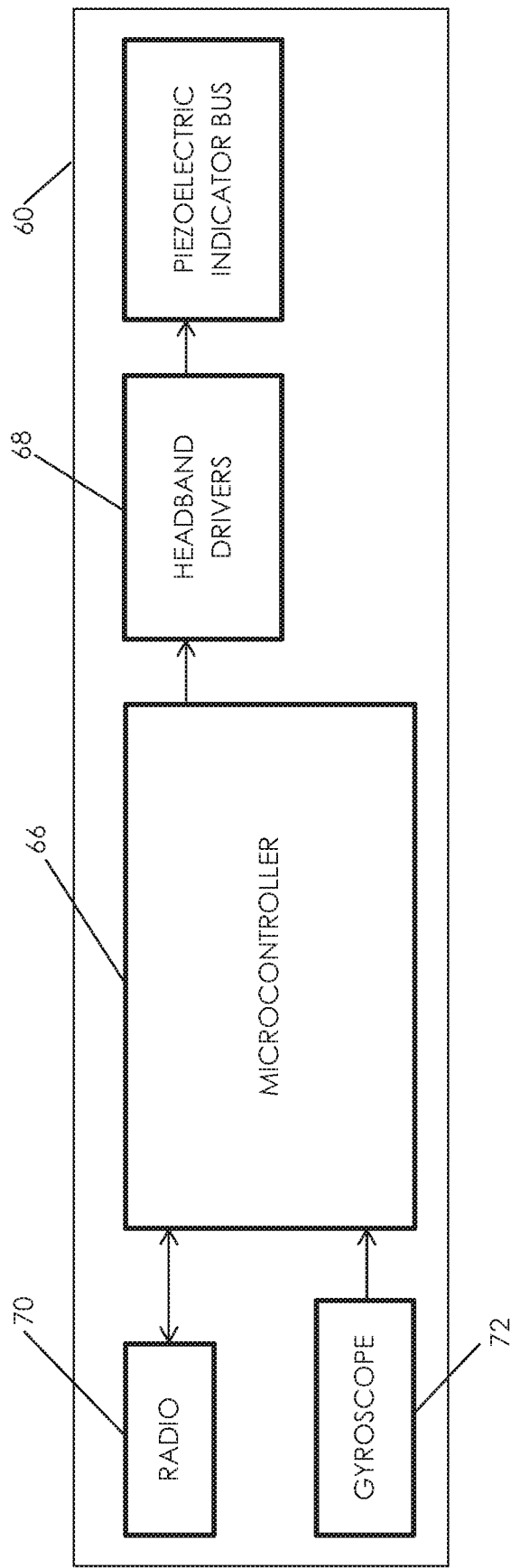
FIG. 4 is a block diagram of the microcontroller in the headband.

FIGS. 3 and 4 show the features of a headband 60. The headband 60 may be formed of elastic material as a conventional headband or may be incorporated into the headband of a hat or helmet. The headband 60 preferably includes a power source 62 such as a battery and a plurality of piezoelectric transducers 64 incorporated into the headband 60 and spaced evenly apart. The piezoelectric transducers 64 provide a vibration which can indicate to the wearer when a course change is needed. FIG. 4 shows a block diagram illustrating the components of the headband 60 including a microcontroller 66 which activates the headband drivers 68 in response to a radio signal received from the control unit 10 which activate one or more of the piezoelectric transducers 64 to alert the wearer of a course change. The headband 60 also includes an RFM69 900 mhz transceiver radio 70. The headband 60 further includes a gyroscope 72 and compass to orient the headband 60 to north. The control unit 10 may also provide a signal to maintain course by activating the piezoelectric transducer 64 that would indicate that the current course is correct. An example of a suitable piezoelectric transducer 64 is manufactured by STEMiNC having Part No. SMMSG25F1000. Alternatively, vibration motors could be used in place of the piezoelectric transducers 64.

In use, the control unit 10 can provide navigational information to a user without the need for the user to look at or even see the display screen 14. The navigational information can be provided auditorily in sounds or speech or through a piezoelectric transducer 64 which provides a vibratory signal. The vibratory signal may be produced through a plurality of piezoelectric transducers located in a headband 60 as shown in FIG. 3 and can preferably be modulated to adjust speed of vibration and intensity. Preferably eight piezoelectric transducers 64 would be included in the headband 60 at spaced apart locations. Each of the piezoelectric transducers 64 is operable independently so that the degree of course change can be indicated by activating one or more of the piezoelectric transducers 64. For example, for a course change from north to east, a piezoelectric transducer 64 that is pointed in the direction of east would vibrate, regardless of the orientation of the headband 60. Alternatively, the vibratory signal may be produced by bone transmitters worn on the user's cheeks or in belt or garment.

This system provides an apparatus and method that allows individuals with impaired vision to navigate sailboats in open water or hike in terrain without paths. The control unit 10 can also be used by individuals who find it is more convenient or useful to hear or feel a navigational signal than to read it. In practice, the control unit 10 can be calibrated to indicate the heading at a user set frequency down to the nearest 0.1 degree to allow for precise navigation. The control unit 10 is programmed to use GPS information to calculate distances between user programmable waypoints, allowing the user to navigate from their current location to each waypoint.

An important feature is the ability of the system to provide a user with multiple informational inputs simultaneously. For example, the input for the direction to the next mark or waypoint can be a steady tone or vibration at a preset time period, say every two seconds. Additionally, another input by either tone or vibration could be set as the direction of the bow of the boat. In this instance the direction the bow of the boat is pointing could be a different tone or lighter vibration than the input for the direction to the next mark and could also be a double tone or double vibration. Further, the location of another boat could be indicated for example by a faster set of tones or beeps or having a different pitch or a quick vibration on the headband. If another boat was passing behind the user's boat, the vibrations in the headband 60 could not only vibrate quickly in a repetitive manner, but could also move about the headband to give the user an indication of the other boat's speed and direction. Furthermore, the control unit 10 could be programmed to provide information about an adjacent boat auditorily including identification of the other boat or sailor.

When the navigation system is used by a number of participants in a sailboat race, the control units 10 can be networked together by the radios. Location, speed and acceleration of each control unit 10 used by each of the participants can be determined to help avoid collisions with other participants. In the networked system, one of the control units 10 would be the master control unit and the other networked units can communicate with each other by radio and therefore be synchronized in location, speed, acceleration and course. Thus, by using a single GPS locator, the GPS location accuracy would be improved since all racers would have the same GPS offset. The networked system would also have built in safeguards such as a safe distance monitor to provide a warning before boats would collide. Offset to avoid collisions is enhanced by the use of radio frequency analysis between boats to precisely determine distances. The amount of offset or safety zone between boats can be adjusted according to weather and sea conditions and sailor skill. Additionally, the marks for the course can have a control unit 10 installed so that precise location of the mark relative to a user's control unit 10 can be determined.

In another preferred embodiment, the control unit 10 using Bluetooth sends the navigation sound signal to a smartphone having an app that is compatible with the control unit programming and the navigational sound is played through the smartphone.

An alternative use for the system would be in underwater applications such as scuba diving at night or in murky water where visibility is limited.

The programming code for the control unit 10 is preferably written in C using the MPLAB XC16 compiler. The code contains the communication protocols between instruments, streaming data from memory, handling all inputs, and using a DAC to play audio waveform files. External applications written in LabVIEW were built to create flash memory layout, as well as interface with the microcontroller over USB. The USB protocol handles debugging functions as well as programming the flash memory with audio information and data.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as maybe applied to the central features hereinbefore set forth, and fall within the scope of the invention and the limits of the appended claims.

I claim:

1. A networked sensory augmentation system for use in navigation by a plurality of sailboats being steered by sailboat racers having visual impairment comprising:
   a) each of said plurality of sailboats having a programmable control unit networked with each of said plurality of sailboats;
   b) each programmable control unit includes a GPS receiver and is configured to retain at least a first programmable waypoint and calculate each of said plurality of sailboats' distance from said first programmable waypoint and said programmable control unit in each of said sailboats being configured to determine a direction of travel necessary to reach said first programmable waypoint;
   c) each of said programmable control units further includes a first radio transceiver for sending and receiving radio signals and each of said programmable control units are configured to calculate the distance for each of said plurality of sailboats from each other;
   d) a wearable device having a second radio transceiver and a plurality of tactile sensory inputs for producing tactile sensations at spaced apart locations on a wearer of said wearable device;
   e) each of said programmable control units being configured to send a radio signal to said wearable device for activating at least one of said plurality of tactile sensory inputs to assist a sailboat racer to maintain a course toward a waypoint.

2. The networked sensory augmentation system as set forth in claim 1, wherein said programmable control unit may be programmed by the user to set a delay of the radio signal.

3. The networked sensory augmentation system as set forth in claim 1, wherein the wearable device includes a headband for supporting said plurality of tactile sensory inputs.

4. The networked sensory augmentation system as set forth in claim 2, wherein setting said delay of the radio signal includes setting how far off course to said first programmable waypoint a sailboat racer may travel before the programmable control unit produces a radio signal to activate at least one of said tactile sensory inputs.

5. The networked sensory augmentation system as set forth in claim 4, wherein said delay of the radio signal may adjusted.

6. The networked sensory augmentation system as set forth in claim 5, wherein said delay of the radio signal may be as low as 0.1 degrees.

7. The networked sensory augmentation system as set forth in claim 1, wherein said tactile sensory input is a least one piezo transducer.

8. The networked sensory augmentation system as set forth in claim 1, wherein each programmable control unit further includes an electronic compass having a magnetometer, accelerometer and a gyroscope for determining a course heading.

9. The networked sensory augmentation system as set forth in claim 8, wherein each programmable control unit can determine distance, speed, direction of travel and acceleration of other programmable control units in said network.

10. A sensory augmentation system for use in navigation comprising:
    a) a control unit including a GPS receiver and is configured to retain at least a first programmable waypoint and calculate distance from said control unit to said first programmable waypoint and said control unit being configured to determine a direction of travel necessary to reach said first programmable waypoint;
    b) said control units further includes a first radio transceiver for sending and receiving radio signals;
    c) a wearable device having a second radio transceiver and a plurality of tactile sensory inputs for producing tactile sensations at spaced apart locations on a wearer of said wearable device;
    d) said control unit being configured to send a radio signal to said wearable device for activating at least one of said plurality of tactile sensory inputs to assist a user to maintain a course toward a waypoint.

11. The sensory augmentation system as set forth in claim 10, wherein said control unit may be programmed by the user to set a delay of the radio signal.

12. The sensory augmentation system as set forth in claim 10, wherein the wearable device includes a headband for supporting said plurality of tactile sensory inputs.

13. The sensory augmentation system as set forth in claim 11, wherein setting said delay of the radio signal includes setting how far off course to said first programmable waypoint a user may travel before the control unit produces a radio signal to activate at least one of said tactile sensory inputs.

14. The sensory augmentation system as set forth in claim 13, wherein said delay of the radio signal may adjusted.

15. The sensory augmentation system as set forth in claim 14, wherein said delay of the radio signal may be as low as 0.1 degrees.

16. The sensory augmentation system as set forth in claim 10, wherein said tactile sensory input is a least one piezo transducer.

17. The sensory augmentation system as set forth in claim 10, wherein each control unit further includes an electronic compass having a magnetometer, accelerometer and a gyroscope for determining a course heading.

18. The sensory augmentation system as set forth in claim 17, wherein each control unit can determine its distance from a waypoint, speed, direction of travel and acceleration.

19. A method for providing direction of travel information to a user comprising:
   a) providing a wearable device having sensory augmentation features for indicating direction of travel;
   b) providing a control unit having GPS capability and a compass;
   c) configuring said control unit to retain at least a first programmable waypoint and calculating a distance from said control unit to said first programmable waypoint and configuring said control unit to determine a direction of travel necessary to reach said first programmable waypoint; and
   d) configuring said control unit to send a radio signal to said wearable device for activating at least one of said sensory augmentation features to assist a user to maintain a course toward a waypoint.

20. The method as set forth in claim 19 further comprising the step of:
   a) providing the wearable device with a gyroscope.

* * * * *